United States Patent [19]

Spivack et al.

[11] Patent Number: 4,508,865

[45] Date of Patent: Apr. 2, 1985

[54] S-(4-HYDROXYPHENYL)THIOCARBOXYLIC ESTER ANTIOXIDANTS

[75] Inventors: John D. Spivack; Stephen D. Pastor, both of Spring Valley, N.Y.

[73] Assignee: Ciba-Geigy Corporation, Ardsley, N.Y.

[21] Appl. No.: 518,561

[22] Filed: Jul. 29, 1983

[51] Int. Cl.³ .................. C08K 5/36; C07C 153/09
[52] U.S. Cl. .......................... 524/283; 260/455 R
[58] Field of Search .................. 524/283, 330, 331; 260/455 R

[56] References Cited

U.S. PATENT DOCUMENTS

| | | | |
|---|---|---|---|
| 1,949,240 | 2/1934 | Bunbury et al. | 524/330 |
| 3,103,500 | 9/1963 | Tholstrup et al. | 524/330 |
| 3,810,929 | 5/1974 | Song | 524/283 |
| 4,128,530 | 12/1978 | Cottman | 524/330 |

FOREIGN PATENT DOCUMENTS 42-6332 3/1967 Japan .
49-116036 11/1974 Japan .

OTHER PUBLICATIONS

Nakanishi et al., Chemical Abstracts, 67, 73382u (1967).

Primary Examiner—Veronica P. Hoke
Attorney, Agent, or Firm—Luther A. R. Hall; Harry Falber

[57] ABSTRACT

The title compounds correspond to the formula

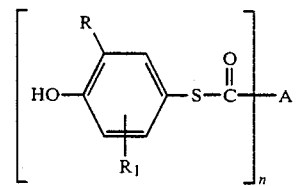

and are useful as stabilizers for organic polymers and lubricating oils to counteract the degradative effects of heat, light and air.

11 Claims, No Drawings

S-(4-HYDROXYPHENYL)THIOCARBOXYLIC ESTER ANTIOXIDANTS

Organic polymeric materials such as plastics and resins, and lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined the thioester derivatives of this invention possess an unusual combination of desirable properties which make them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of cross-linking, crazing, discoloration, odor formation and exudation are basic requirements.

A number of mercaptophenol derivatives have been previously disclosed. Many of these derivatives are, however, hydroxyphenylthio alkanoate esters. Thioesters are disclosed in Japan Kokai No. 67 6332 [S,S'-bis(3,5-di-tert.butyl-4-hydroxyphenyl)-dithiopropionate] and in Japan Kokai No. 74 116,036 [S,S'-bis(3,5-di-tert.butyl-4-hydroxyphenyl)dithioacetate] as antioxidants.

It is the primary object of this invention to provide a class of thioester derivatives which exhibit a broad range of improved stabilization performance characteristics.

Various other objects and advantages of this invention will become evident from the following description thereof.

The compounds of this invention correspond to the formula

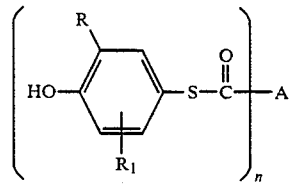

wherein

R and $R_1$ are independently hydrogen, alkyl of 1 to 12 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms;

n is 1–2, and when n=1, A is alkyl of 1 to 30 carbon atoms, cycloalkyl of 5 to 6 carbon atoms, phenyl or lower alkyl substituted benzyl; and when n=2, A is alkylene of from 1 to 10 carbon atoms, cycloalkylene of 5 to 6 carbon atoms, arylene, biphenylene or hydroxy-substituted arylene.

Preferred compounds within the above structure are those wherein both R and $R_1$ are in the ortho position to the hydroxy group. The R and $R_1$ groups are preferably straight-chain or branched alkyl with 1 to 8 carbon atoms, such a methyl, n-butyl, sec-butyl, tert-butyl, tert-pentyl 2-ethylhexyl, n-octyl and 1,1,3,3-tetramethylbutyl. The groups methyl, tert-butyl, tert-pentyl and 1,1,3,3-tetramethylbutyl are especially preferred. Also especially preferred, as previously noted, is for the $R_1$ group to be in the ortho position to the hydroxy group, particularly if $R_1$ is tert-alkyl.

When R and $R_1$ are aralkyl, they represent benzyl, alpha-methylbenzyl or alpha, alpha-dimethylbenzyl. Aryl or arylene substituents are generally derived from phenyl, tolyl, mesityl, xylyl and 1- and 2-naphthyl.

Preferred compounds are those wherein n=2, A is alkylene of 1 to 10 carbon atoms, preferably 4 to 8 carbon atoms, further preferably 8 carbon atoms, or phenylene, and R and $R_1$ are tert.butyl.

The compounds of this invention can be prepared by reacting the appropriate mercaptophenol with the appropriate acid halide in the presence of a proton acceptor and removing the evolved hydrogen halide. Typical proton acceptors include lithium salts, tertiary amines, alkali metals, alkali metal and alkaline earth metal hydroxides, carbonates, and the like. The reaction is conducted in the presence of a solvent including aromatic solvents such as benzene, toluene, xylene, and the like, or aliphatic solvents such as heptane. The reaction temperature generally ranges from 0° to 70° C. The starting materials utilized to prepare these compounds are items of commerce or can be prepared by known methods.

Compounds of this invention are particularly effective in stabilizing organic materials such as plastics, polymers and resins in addition to mineral and synthetic fluids such as lubricating oils, circulating oils, etc.

Substrates in which the compounds of this invention are particularly useful are polyolefins such as polyethylene and polypropylene, polystyrene, including impact polystyrene, ABS resin, SBR, isoprene, as well as natural rubber, polyesters including polyetheylene terephthalate and polybutylene terephthalate, including copolymers, and lubricating oils such as those derived from mineral oil.

In general polymers which can be stabilized include:

1. Polymers of monooelfines and diolefines, for example polyethylene (which optionally can be crosslinked), polypropylene, polyisobutylene, polybutene-1, polymethylpentene-1, polyisoprene or polybutadiene as well as polymers of cycloolefins, for instance of cyclopentene or norbornene.

2. Mixtures of the polymers mentioned under (1), for example mixtures of polypropylene with polyisobutylene.

3. Copolymers of monoolefines and diolefines with each other or with other vinyl monomers, such as, for example, ethylene/propylene, propyene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or α-methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamid or poly-m-phenylene isophthalamide, as well as copolymers thereof with polyethers, such as for instance, with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2,-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/-butadiene copolymers.

In general the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrat]
di-(3-tert.butyl-4-hydroxy-5-methylphenyl)-dicyclopentadien
di-[2-(3'-tert.butyl-2'-hydroxy-5'-methyl-benzyl)-6-tert.butyl-4-methylphenyl]-terephthalate.

1.5. Benzylcompounds, for example,
1,3,5-tri-(3,5-di-tert.butyl-4-hydroxybenzyl)-2,4,6-trimethyl-benzene-di-(3,5-di-tert.butyl-4-hydroxybenzyl)-sulfide
3,5-di-tert.butyl-4-hydroxybenzyl-mercapto-acetic acid-isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-tria-zine
octyl-N-(3,5-di-tert.butyl-4-hydroxyphenyl)-carbaminate 1.7. Esters of β-(3,5-di-tert.butyl-4-hydroxyphenyl)-propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Ester of β-(5-tert.butyl-4-hydroxy-3-methylphenyl)propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.9. Amides of β-(3,5-di-tert.butyl-4-hydroxyphenyl)-propionic acid for example,
N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV Absorbers and Light Stabilisers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3', 5'-di-tert.butyl-, 5-chloro-3'-tert. butyl-5'-methyl-, 3'-sec.butyl-5'- tert.butyl-, 4'-octoxy-,3',5'-di-tert.amyl-, 3',5'-bis-(α,α-dimethylbenzyl)-derivative.

2.2. 2-Hydroxy-benzophenones, for example, the 4-hydroxy-,4-methoxy-, 4-octoxy, 4-decyloxy-, 4-dodecyloxy-, 4-benzyloxy, 4,2',4'-trihydroxy- and 2'-hydroxy-4,4'-dimethoxyderivative.

2.3. Esters of optionally substituted benzoic acids for example, phenyl salicylate, 4-tert.butyl-phenylsalicilate, octylphenyl salicylate, dibenzoylresorcinol, bis-(4-tert.butylbenzoyl)-resorcinol, benzoylresorcinol,3,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzyl-phosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethyl-piperazinone).

2.7. Oxalic acid diamides, for example, 4,4'-di-octyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho-and para-methoxy- as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythrit diphosphite, tris-(2,4-di-tert.butylphenyl) phosphite, di-isodecylpentaerythrit diphosphite, di-(2,4-di-tert.butylphenyl)pentaerythrit diphosphite, tristearylsorbite triphosphite, tetrakis-(2,4-di-tert.butylphenyl)-4,4'-biphenylylen diphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrit-tetrakis-(β-dodecylmercapto)-propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate. antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE 1

S,S'-Bis(3,5-di-tert-butyl-4-hydroxyphenyl)dithioadipate

A flame dried flask, under nitrogen, was charged with 3.84 grams (0.021 mol) of adipoyl chloride, 50 ml toluene and 50 ml heptane. The resultant mixture was cooled in an ice bath and a solution of 10.0 grams (0.042 mol) of 2,6-di-tert-butyl-4-mercaptophenol and 4.25 grams (0.042 mol) of triethylamine in 50 ml toluene and 50 ml heptane was added dropwise. After the addition was complete, the resultant suspension was warmed to room temperature and stirred until the disappearance of the starting mercaptan was indicated by thin layer chromatography. The mixture was then filtered and the filter cake washed twice with 50 ml each of warm toluene. The combined filtrates were concentrated in vacuo and the residue recrystallized from acetonitrile to yield 9.8 g (80%) of white crystals, mp 140°–143° C.

Anal. Calcd. for $C_{34}H_{50}O_4S_2$: C, 69.6; H, 8.6; S, 10.9. Found: C, 69.9; H, 9.0; S, 11.1.

EXAMPLE 2

S,S'-Bis(3,5-di-tert-butyl-4-hydroxyphenyl)dithiosebacate

The procedure of Example 1 was repeated utilizing 5.02 grams (0.021 mol) of sebacoyl chloride, 10.0 grams (0.042 mol) of 2,6-di-tert-butyl-4-mercaptophenol, 4.25 grams (0.042 mol) of triethylamine, 100 ml of toluene and 100 ml of heptane. Purification of the residue by recrystallization from acetonitrile gave 6.2 grams (46%) of white powder, mp 82°–85° C.

Anal. Calcd. for $C_{38}H_{58}O_4S_2$: C, 71.0; H, 9.1; S, 10.0 Found: C, 70.8; H, 9.1; S, 9.8.

EXAMPLE 3

S,S'-Bis(3,5-di-tert-butyl-4-hydroxyphenyl)dithioterephthalate

The procedure of Example 1 was repeated utilizing 4.26 grams (0.021 mol) of terephthaloyl chloride, 10.0 grams (0.042 mol) of 2,6-di-tert-butyl-4-mercaptophenol, 4.25 grams (0.042 mol) of triethylamine and 400 ml of toluene. Purification of the residue by recrystallization from methyl ethyl ketone gave 10.0 grams (78%) of off-white crystals, mp 310° C.

Anal. Cald. for $C_{36}H_{46}O_4S_2$: C, 71.3; H, 7.6; S, 10.6. Found: C, 71.3; H, 7.8; S, 10.7.

EXAMPLE 4

This example illustrate the stabilizing effectiveness of the instant stabilizer combination in impact polystyrene.

In the laboratory procedure utilized herein, a solution of eight weight percent polybutadiene rubber (Firestone-DIENE 55) dissolved in styrene monomer was prepared on a roller mill. The 0.1%, by weight, amount of stabilizer was also introduced at this point. 500 ppm of zinc stearate was added to aid in removing the sample from the bottle after the polymerization. The bottle was screwed into the polymerization apparatus which was equipped with a double helical ribbon stirrer. Since most commercial IPS bulk polymerizations are thermally initiated processes, no initiator was used in the laboratory process. A nitrogen atmosphere was established and then the reactor was heated to 121° C. within ½ hour. Heating continued at 121° C. with efficient stirring until there was a 30 to 35% monomer conversion (~2½ hours). The stirring rate was controlled to yield a two to four μm rubber particle size. The bottles were removed from the polymerization apparatus, blanketed with nitrogen, capped, and then placed in a fluidized bed sand bath to complete the polymerization. The bottles were heated in the bath in the following fashion: one hour at 100° C. to equilibrate the temperature, one hour to reach 140° C. and then an additional eight hours with the temperature increasing at the rate of 10° C. per hour to a maximum of 220° C. After the resin had cooled, the bottle was broken and the glass was removed. The average weight of the polymer block was slightly over 600 grams. The block was then placed into a vacuum over at 200° C. and a vacuum of 1 mm applied as the polymer was heated for 45 minutes in order to remove all volatiles. The block was then removed from the oven, immediately placed in a heated (205° C.) hydraulic press and then pressed into a thick slab between two sheets of aluminum foil (three minutes heating, five minutes in a cold press). The slab was split with a band saw and the pieces were granulated.

All batches were extruded at 205° C. and then pelletized. The pellets were compression molded at 205° C. into 125 mil tensile bars. The bars were then aged at 150° C. on glass plates placed on rotating shelves in a forced air oven. Other tensile bars were aged at 80° C. suspended from rotating shelves in a forced air oven. The specimen yellowness index was determined on the bars at various intervals according to ASTM D 1925-63T. Correspondingly, the bars were periodically measured for percent elongation in the Instron Tensile Testing Apparatus (Instron Engineering Corporation, Massachusetts) at a pull rate of 5 mm per minute according to ASTM D638.

| Additive | Oven Aged Samples @ 80° C. % Elongation Hours at 80° C. | | | | | Oven Aged Samples @ 150° C. % Elongation Hours at 150° C. | | | | |
|---|---|---|---|---|---|---|---|---|---|---|
| | 0 | 300 | 600 | 900 | 1200 | 0 | ½ | 1 | 1½ | 2 |
| None | 33 | 9 | 3 | 3 | 3 | 33 | 7 | 7 | 3 | 3 |
| Compound of Example 2 | 50 | 22 | 10 | 6 | 4 | 50 | 51 | 14 | 7 | 6 |
| | Yellowness Index | | | | | | | | | |
| None | 7 | 14 | 45 | 59 | — | 7 | 18 | 30 | 38 | 43 |
| Compound of Example 2 | 9 | 11 | 21 | 54 | — | 9 | 8 | 17 | 19 | 25 |

EXAMPLE 5

Unstabilized polypropylene powder (Hercules Profax 6501) was thoroughly blended with 0.2%, by weight, of additive. The blended materials were then milled on a two roll mill at 182° C. for five minutes, after which time the stabilized polypropylene was sheeted from the mill and allowed to cool. The milled polypropylene was then cut into pieces and compression molded on a hydraulic press at 220° C. (175 psi) for 5 mil films. The sample was exposed in a fluorescent sunlight/black light chamber to failure, failure being defined as the showing of the first signs of decomposition (cracking or brown edges).

| Additive | Hours to Faliure |
|---|---|
| None | 200–300 |
| Compound of Example 1 | 500 |
| Compound of Example 2 | 450 |
| Compound of Example 3 | 400 |

EXAMPLE 6

The oxidation stability of milled polypropylene (see Ex. 5) containing 0.2% of the instant stabilizers and of milled polypropylene-containing synergized formulations of 0.1% of the instant stabilizers in the presence of 0.3% distearylthiopropionate was determined by exposing plaques of 25 mil thickness to air in a forced draft oven at 150° C. The plaques were considered to have failed on showing the first signs of decomposition (e.g. cracking or brown edges).

| Antioxidant | Time to Failure (hours) | |
|---|---|---|
| | 0.2% | 0.1% + 0.3% DSTDP* |
| Base Resin | <20 | <20 |
| Compound of Example 1 | 310 | 570 |
| Compound of Example 2 | 520 | 1130 |
| Compound of Example 3 | 320 | 1300 |

*Distearyl thiodipropionate

The various data indicate the excellent stabilizing performance of the instant compounds.

Summarizing, it is seen that this invention provides a novel class of stabilizer compounds. Variations may be made in proportions, procedures, and materials without departing from the scope of the invention as defined by the following claims.

What is claimed is:

1. A compound of the formula

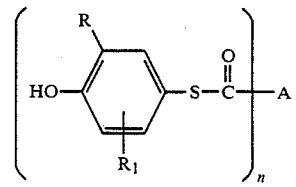

wherein
R and R₁ are in the ortho position to the hydroxyl group and are independently hydrogen, alkyl of 1 to 12 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms;
n=2, and A is alkylene of from 1 to 10 carbon atoms, cycloalkylene of 5 to 6 carbon atoms arylene, biphenylene or hydroxy-substituted arylene.

2. The compound of claim 1, wherein R and $R_1$ are alkyl of from 1 to 8 carbon atoms.

3. The compound of claim 3, wherein R and $R_1$ are tert.butyl.

4. The compound of claim 1, wherein A is alkylene of 4 to 8 carbon atoms or phenylene.

5. S,S'-bis(3,5-di-tert.butyl-4-hydroxyphenyl)dithioadipate according to claim 1.

6. S,S'-bis(3,5-di-tert.butyl-4-hydroxyphenyl)dithiosebacate according to claim 1.

7. S,S'-bis(3,5-di-tert.butyl-4-hydroxyphenyl)dithioterephthalate according to claim 1.

8. A composition of matter comprising an organic material subject to oxidative, thermal and actinic degradation stabilized with an effective stabilizing amount of a compound of claim 1.

9. The composition of claim 8, wherein the organic material is a synthetic polymer.

10. The composition of claim 9, wherein said polymer is selected from the group consisting of impact polystyrene, acrylonitrile/butadiene/styrene, styrene/butadiene rubber, polyesters and poly-alpha-olefins.

11. A method for stabilizing an organic material against oxidative, thermal and actinic degradation which comprises incorporating into said organic material an effective stabilizing amount of a compound of claim 1.

* * * * *